United States Patent
Goda et al.

(10) Patent No.: US 6,503,598 B1
(45) Date of Patent: Jan. 7, 2003

(54) FLEXIBLE COMPOSITE SHEET FOR DISPOSABLE GARMENT

(75) Inventors: Hiroki Goda, Kagawa-ken (JP); Takayuki Hisanaka, Kagawa-ken (JP)

(73) Assignee: Uni-Charm Corporation, Ehime-Ken (JP)

(*) Notice: Subject to any disclaimer, the term of this patent is extended or adjusted under 35 U.S.C. 154(b) by 38 days.

(21) Appl. No.: 09/694,592

(22) Filed: Oct. 23, 2000

(30) Foreign Application Priority Data

Oct. 29, 1999 (JP) .............................. 11-309053

(51) Int. Cl.[7] .............................................. A61F 13/15
(52) U.S. Cl. ........................ 428/137; 428/131; 428/138; 604/378; 604/379; 604/380; 604/383; 604/385.01; 604/385.101
(58) Field of Search ................................ 428/131, 132, 428/137, 138; 442/362; 604/365, 366, 370, 371, 374, 378, 379, 380, 383, 385.01, 385.101

(56) References Cited

U.S. PATENT DOCUMENTS

| | | | |
|---|---|---|---|
| 2,788,003 A | 4/1957 | Morin | 604/366 |
| 4,637,819 A | 1/1987 | Ouellette et al. | 428/131 |
| 5,613,960 A * | 3/1997 | Mizutani | 604/358 |
| 5,891,119 A | 4/1999 | Ta et al. | 604/365 |
| 6,117,524 A | 9/2000 | Hisanaka et al. | 428/131 |

FOREIGN PATENT DOCUMENTS

| | | | |
|---|---|---|---|
| EP | 0 919 212 A2 | 6/1999 | ........... A61F/13/15 |
| JP | A-62-57551 | 3/1987 | |

* cited by examiner

*Primary Examiner*—Harold Pyon
*Assistant Examiner*—Alicia Chevalier
(74) *Attorney, Agent, or Firm*—Baker & Daniels

(57) ABSTRACT

A composite sheet adapted to be used as a stock material for disposable garments comprises a film-like upper layer and a lower layer formed by a fibrous assembly. The upper layer is formed with a first surface region having plane zones and aperture arrays and a second surface region in the form of a depression. The lower layer has its density higher in a region immediately underlying the second surface region than in a region immediately underlying the first surface region. The composite sheet including such constituent features is suitable as stock material for disposable garments which require a soft touch and a rapid permeation of body fluids discharged on the garments.

9 Claims, 4 Drawing Sheets

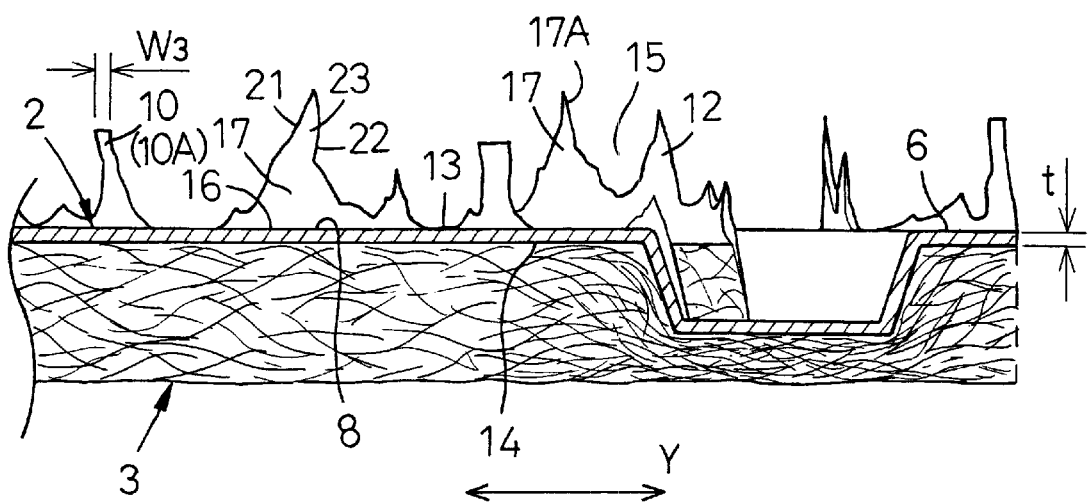
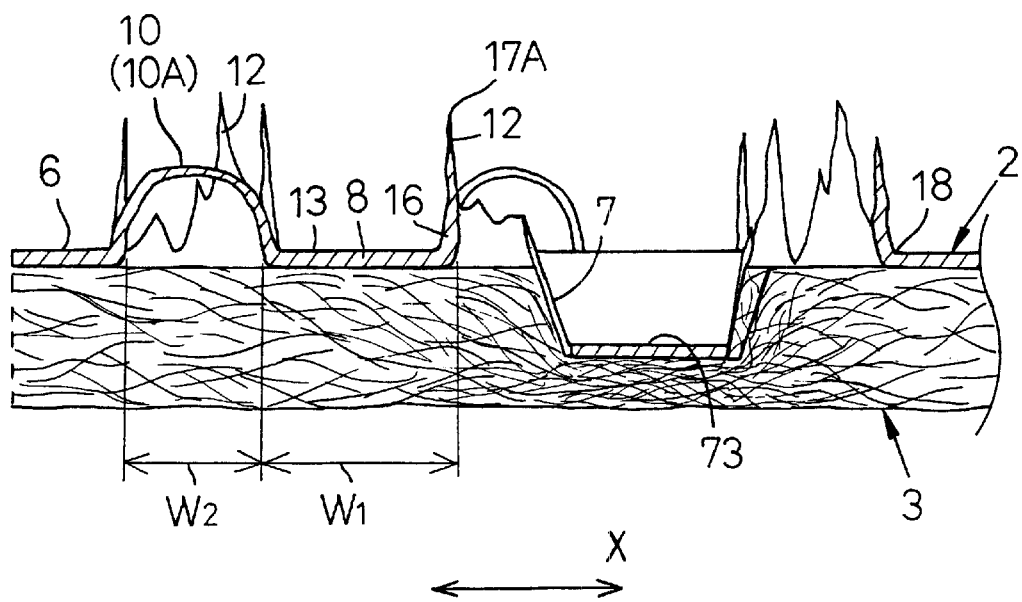

FLEXIBLE COMPOSITE SHEET FOR DISPOSABLE GARMENT

BACKGROUND OF THE INVENTION

This invention relates to a flexible sheet suitable as a stock material for disposable garments, particularly for disposable body fluid absorbent garments such as disposable diapers, sanitary napkins or the like.

FIG. 5 in the accompanying drawings is a perspective view showing a plastic sheet 110 described in Japanese Patent Application Disclosure No. 1987-57551, which is finely apertured and presents a soft touch. This plastic sheet 110 is intended to be used as top—or backsheets of disposable diapers and is obtained by placing a relatively thin plastic sheet as raw sheet on a belt of mesh wire and then subjecting this raw sheet to a process using high pressure liquid jets.

The plastic sheet 110 processed in this manner is formed on its surface intended to come in contact with a wearer's skin with a plurality of cylindrical protuberances 120 which are, in turn, formed at their tops with fine apertures 125 and petal-like fringes rising from peripheral edges of the respective apertures 125. Such a sheet 110 is described as lusterless and offers a cloth-like soft touch.

Certainly a cloth-like soft touch will be offered by the cylindrical protuberances 120 and the petal-like fringes formed on the tops of the respective protuberances 120 when the plastic sheet 110 is used, for example, as a liquid-pervious topsheet of a disposable diaper. However, it will be difficult for body fluids discharged onto the topsheet to be rapidly guided into the respective apertures 125 since the apertures 125 are formed on the tops of the respective protuberances 120 and the protuberances 120 will obstruct the body fluids from being rapidly guided into the apertures 125. Moreover, the apertures 125 of the plastic sheet 110 are spaced from a liquid-absorbent core usually underlying the topsheet in the conventional disposable diapers by a distance corresponding to the height of the protuberances 120. In consequence, it is also difficult for the body fluids to be rapidly absorbed by the liquid-absorbent core.

SUMMARY OF THE INVENTION

It is an object of this invention to provide a flexible sheet presenting a soft touch into which body fluids can rapidly permeate.

According to this invention, there is provided a flexible composite sheet having upper and lower layers adapted to be used for a disposable garment which comprises the following constituent features.

The upper layer of the composite sheet is formed by a thermoplastic synthetic resin film and has a first surface region and a second surface region. The first surface region comprises a plurality of substantially plane zones extending parallel one to another in one direction, each of the plane zones having upper and lower surfaces, a thickness of 0.001~0.05 and a width of 0.03~1 mm and a plurality of aperture arrays defined between each pair of adjacent ones of the plane zones, each of the aperture arrays including a plurality of apertures arranged intermittently in the one direction and each the aperture having a width of 0.03~1 mm and a length corresponding to at least 1.5 times of the width. The plane zones and the aperture arrays are alternately arranged in a direction transverse to the one direction so that each pair of the plane zones adjacent to each other with the aperture array therebetween are connected to each other by a plurality of bridge zones extending from these two plane zones across the aperture array. The Plane zones are provided at least along regions of peripheral edges thereof defining the apertures extending in the one direction with a plurality of rising zones rising from the plane zones so as to irregularly undulate and troughs defined between respective pairs of the rising zones being adjacent to each other in the one direction. The second surface region is formed by depressing the plane zone downward from its upper surface toward its lower surface by a depth of at least 0.1 mm. The lower layer of the composite sheet is formed by a fibrous assembly having a substantially uniform basis weight and bonded to the lower surface of the upper layer at least over the second surface region wherein the fibrous assembly contains thermoplastic synthetic fibers of at least 30% by weight and has its density higher in region immediately underlying the second surface region than in region immediately underlying the first surface region of the upper layer.

In spite of the material for the upper layer being a thermoplastic synthetic resin film, the composite sheet according to this invention presents a cloth-like soft touch which is provided by a plurality of fine rising zones formed on the upper layer. When this composite sheet is used as the topsheet of a body fluid absorbent garment, body fluid discharged onto the upper layer is smoothly guided along the troughs defined between respective pairs of the adjacent rising zones into the apertures formed in the upper layer and then absorbed into the fibrous assembly forming the lower layer. The lower layer has its density progressively increasing from the zones underlying the respective first surface regions toward the zones underlying the respective second surface regions until the density reaches the maximum value in the vicinity of the lower surface of the lower layer. Thus, the body fluid once having been absorbed into the lower layer rapidly moves away from the garment wearer's skin toward the lower surface of the lower layer.

As will be apparent from the foregoing description, the body fluid absorbent garment using the inventive composite sheet as the liquid-pervious topsheet not only presents a comfortable touch but also protects the garment wearer from uncomfortable feeling of wetness because the body fluid discharged onto the topsheet can be rapidly absorbed away from the garment wearer's skin.

BRIEF DESCRIPTION OF THE DRAWINGS

FIG. 2 is a sectional view taken along line II—II in FIG. 1;

FIG. 3 is a sectional view taken along line III—III in FIG. 1;

DETAILED DESCRIPTION OF THE PREFERRED EMBODIMENTS

Details of a flexible composite sheet according to this invention used for disposable garments will be more fully understood from the description given hereunder with reference to the accompanying drawings.

Figure 1:
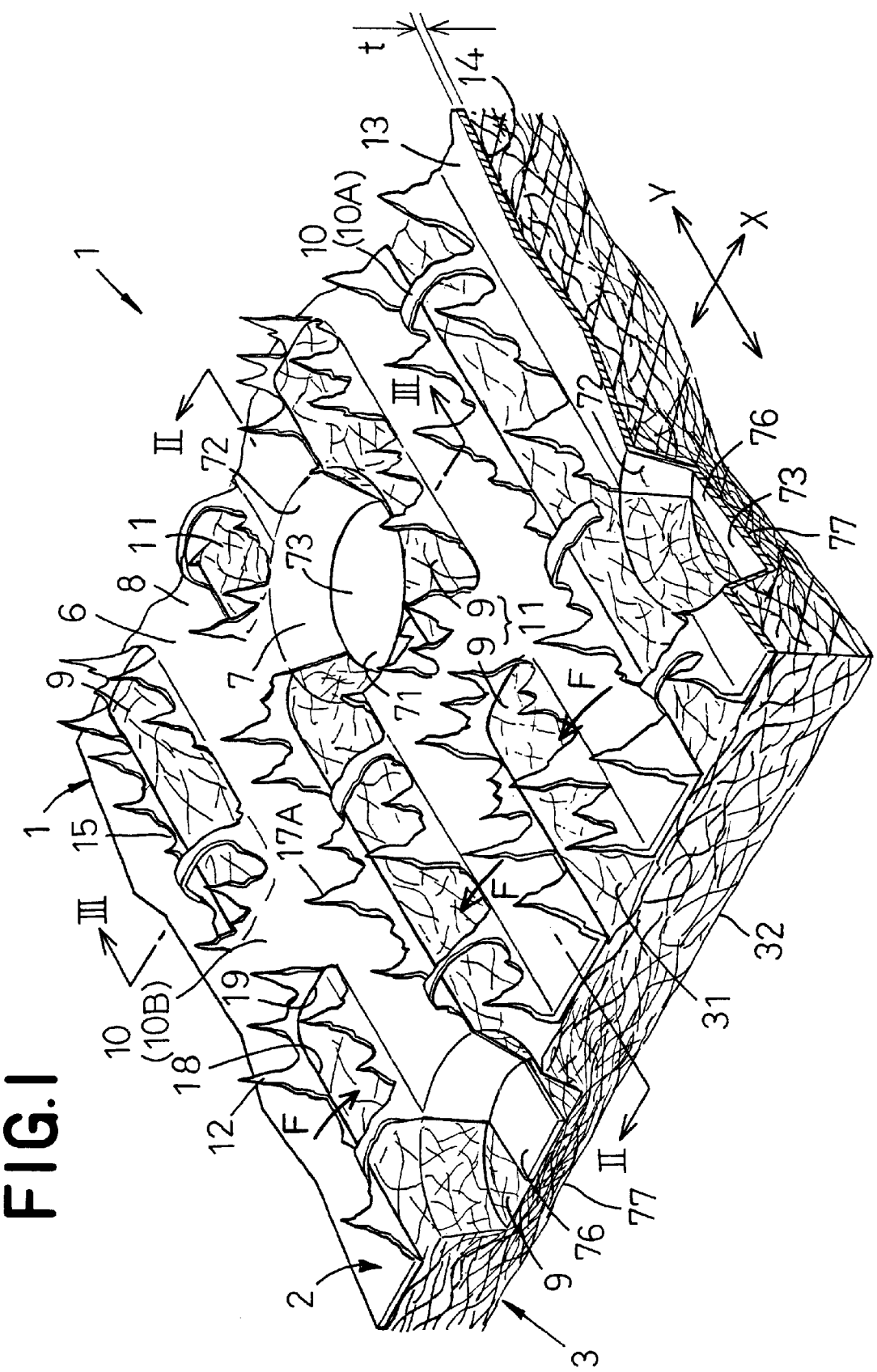
FIG. 1 is a perspective view depicting one embodiment of a composite sheet according to this invention.

A composite sheet 1 depicted by FIG. 1 in a perspective view comprises an upper layer 2 and a lower layer 3.

The upper layer 2 is formed by a thermoplastic synthetic resin film processed to define a first surface region 6 and a second surface region 7. The first surface region 6 having a plurality of plane zones 8 extending parallel one to another in a direction indicated by a double-headed arrow Y and a plurality of elongate aperture arrays 11 extending parallel one to another in the direction Y, each comprises a plurality of apertures 9.

Each of the plane zones 8 has an upper surface 13 and a lower surface 14 and each aperture array 11 comprising the apertures 9 lies between each pair of the plane zones 8, 8 being adjacent to each other in a direction indicated by a double-headed arrow X which is orthogonal to the direction Y.

In each of the aperture arrays 11, a bridge zone 10 is formed between each pair of the apertures 9, 9 being adjacent to each other in the direction Y so as to connect the pair of the adjacent plane zones 8, 8. Each edge of the plane zone 8 is formed with crest zones 12 rising on the upper surface 13 of the plane zone 8 repetitively in the direction Y and trough zones 15 are formed between the respective pairs of the crest zones 12, 12 being adjacent to each other in the direction Y.

The second surface region 7 is defined by a depression 71 extending downward from the upper surface 13 of the plane zone 8 toward its lower surface 14. The depression 71 shown in FIG. 1 is top-cut and inverse truncated cone-shaped and comprises a side wall 72 extending from the plane zone 8 and a bottom wall 73 extending from the side wall 72. The side wall 72 as well as the bottom wall 73 has an upper surface 76 and a lower surface 77 and some of the apertures 9 extend from the first surface region 6 to the side wall and bottom wall 72, 73.

The lower layer 3 is formed by a fibrous assembly entirely having a substantially uniform basis weight and having an upper surface 31 and a lower surface 32. The upper surface 31 is bonded to the lower surface 14 of the first surface region 6 and/or the lower surface 77 of the second surface region 7, at least the lower surface 77 of the second surface region 7 of the upper layer 2. The lower surface 32 extending on the side opposite to the upper surface 31 is practically plane. The lower layer 3 contains thermoplastic synthetic fibers of at least 30% by weight, preferably 100% by weight and bonded to the lower surface 77 of the upper layer 2 by means of adhesive or heat-sealing technique.

FIGS. 2 and 3 are sectional views taken along lines II—II and III—III, respectively, in FIG. 1. The plane zone 8 of the sheet 1 has a thickness of 0.001~0.05 mm and the aperture 9 is spaced from the adjacent aperture 9 in the direction X by a width $W_1$ of 0.03~1 mm. The aperture 9 has a width $W_2$ of 0.03~1 mm in the direction X and a length in the direction Y corresponding to at least 1.5 times of its width $W_2$. The bridge zones 10 extending across the respective aperture arrays 11 are formed intermittently in the direction Y and some of them identified by reference numeral 10A describe circular arcs which extend from the upper surface 13 of the plane zone 8 to be convex upward or downward and others identified by reference numeral 10B flatly extend between each pair of the adjacent plane zones 8 (See FIG. 1). Preferably, the bridge zone 10 has a width $W_3$ in the direction Y at least of 0.001~2 mm.

The rising zone 12 is formed by a portion of the plane zone 8 defining an edge of the aperture 9 bent upwardly of the upper surface 13 and has a proximal end 16 contiguous to the plane zone 8 and a free end portion 17 extending upward from the proximal end 16. Top edges 17A of the respective free end portions 17 undulate along an edge 18 of the plane zone 8 extending in the direction Y and a trough 15 is defined between each pair of the rising zones 12, 12 being adjacent to each other in the direction Y. A height H of the rising zone 12 as measured from the upper surface 13 of the plane zone 8 to the top edge 17A of the rising zone 12 is preferably less than 1 mm. The top edges 17A undulate, as exemplarily shown in FIG. 2, in the form of repeatedly appearing rectangular regions 23 each comprising an oblique side 21 extending substantially right-and upward, an oblique side 22 extending substantially left-and upward and the proximal end 16 extending the oblique sides 21, 22. The rising zone 12 has a thickness equal to or less than the thickness of the plane zone 8 so that the rising zones 12 may be flexibly deformed as they come in contact with a wearer's skin and thereby provide the surface of the sheet 1 with a velvety feel.

The second surface zone region of the upper layer 2 is formed by locally depressing the first surface region 6 from the upper surface 13 toward the lower surface 14. A depth by which the second surface region 7 is depressed from the upper surface 13 is preferably at least 0.1 mm. While the shape of the second surface region 7 as viewed in its plan view is illustrated to be circular, it should be understood that the region 7 may be of the other shape such as oval or polygonal so far as a circle inscribed therein has the maximum diameter of 5 mm. Each pair of the adjacent second surface regions 7, 7 should be spaced from each other at least by 2 mm. The second surface regions 7 preferably occupy 10~50% of the entire sheet 1.

The lower layer 3 has a basis weight of 5~20 g/m² and this basis weight is substantially uniform all over the sheet 1. The lower layer 3 contains thermoplastic synthetic fibers of at least 30% by weight and may contain, in addition to this, chemical fibers such as rayon fibers and natural fiber such as cotton fibers or pulp fibers. Preferably, the lower layer 3 is formed by a nonwoven fabric made of thermoplastic synthetic fibers or a mixture of thermoplastic fibers and the other fibers. The thermoplastic synthetic fibers preferably have a fineness of 0.11 Dtex~16.5 Dtex and such thermoplastic synthetic fibers includes melt blown fiber also.

The lower layer 3 is bonded to the lower surface 14 of the first surface region 6 and/or the lower surface 14 of the second surface region 7, at least to the latter by means of adhesive or sealing technique so that the lower layer 3 may be exposed within the respective apertures 9 of the upper layer 2. The lower layer 3 is compressed in the thickness direction of the composite sheet 1 more densely in the second surface region 7 than in the first surface region 6 so that the lower layer 3 may have its density progressively increased from the first surface region 6 toward the second surface region 7 until the density increases to the maximum value immediately under the bottom wall 73 of the second surface region 7. The part of the composite sheet 1 comprising the first surface region 6 of the upper layer 2 and the part of the lower layer 3 underlying the first surface region 6 of the upper layer 2 has a density $d_1$ of 0.01~0.3 g/cm³, preferably of 0.03~0.15 g/cm³ while the part of the composite sheet 1 comprising the second surface region 7 of the upper layer 2 and the part of the lower layer 3 underlying the second surface region 7 of the upper layer 2 has a density $d_2$ of 0.05~0.9 g/cm³, preferably of 0.1~0.5 g/cm³. It is essential that the density $d_2$ is always higher than the density $d_1$ and preferably at least 1.2 times of the density $d_1$ or higher.

Depending on the particular application of the composite sheet 1, component fibers of such lower layer 3 is preferably hydrophilic. To meet this requirement, it is also possible to treat hydrophobic thermoplastic synthetic fibers and thereby to make them hydrophilic before use.

When the composite sheet 1 arranged as has been described above is used as a liquid-pervious topsheet in the body fluid absorbent garment such as disposable diapers or sanitary napkins, body fluid, for example, urine discharged onto the plane zones 8 flows into the apertures 9 along the troughs 15 defined between the respective pairs of the rising zones 12 adjacent one to another in the direction Y. For example, referring to FIG. 1, the body fluid is guided into the apertures 9 as indicated by an arrow F and then absorbed in the lower layer 3. In the lower layer 3, the density of the component fibers is progressively increased from the first surface region 6 toward the second surface region 7 so that the body fluid may smoothly move toward the region of the lower layer 3 immediately underlying the second surface region 7, i.e., the body fluid may tend to move from the upper surface 31 toward the lower surface 32 of the lower layer 3. A liquid-absorbent core is usually placed immediately under the topsheet in the aforesaid garment and therefore the body fluid having moved to the lower surface 32 of the lower layer 3 is rapidly absorbed by this core. In the composite sheet 1, the second surface region 7 is defined by a depression and the body fluid having been guided into this depression further moves to the lower layer 3 through the apertures 9 formed in the second surface region 7. In the case of the second surface region 7 being relatively shallow, the body fluid can be easily guided into the apertures 9 formed in the first surface region 6.

The composite sheet 1 functioning as has been described above presents a cloth-like soft touch given by a plurality of rising zones 12 on the upper layer 2 and such characteristic makes the composite sheet 1 suitable as the topsheet of the garment such as a disposable gown used in the medical field which requires a breathability or a combined breathability and liquid-permeability.

Figure 4:
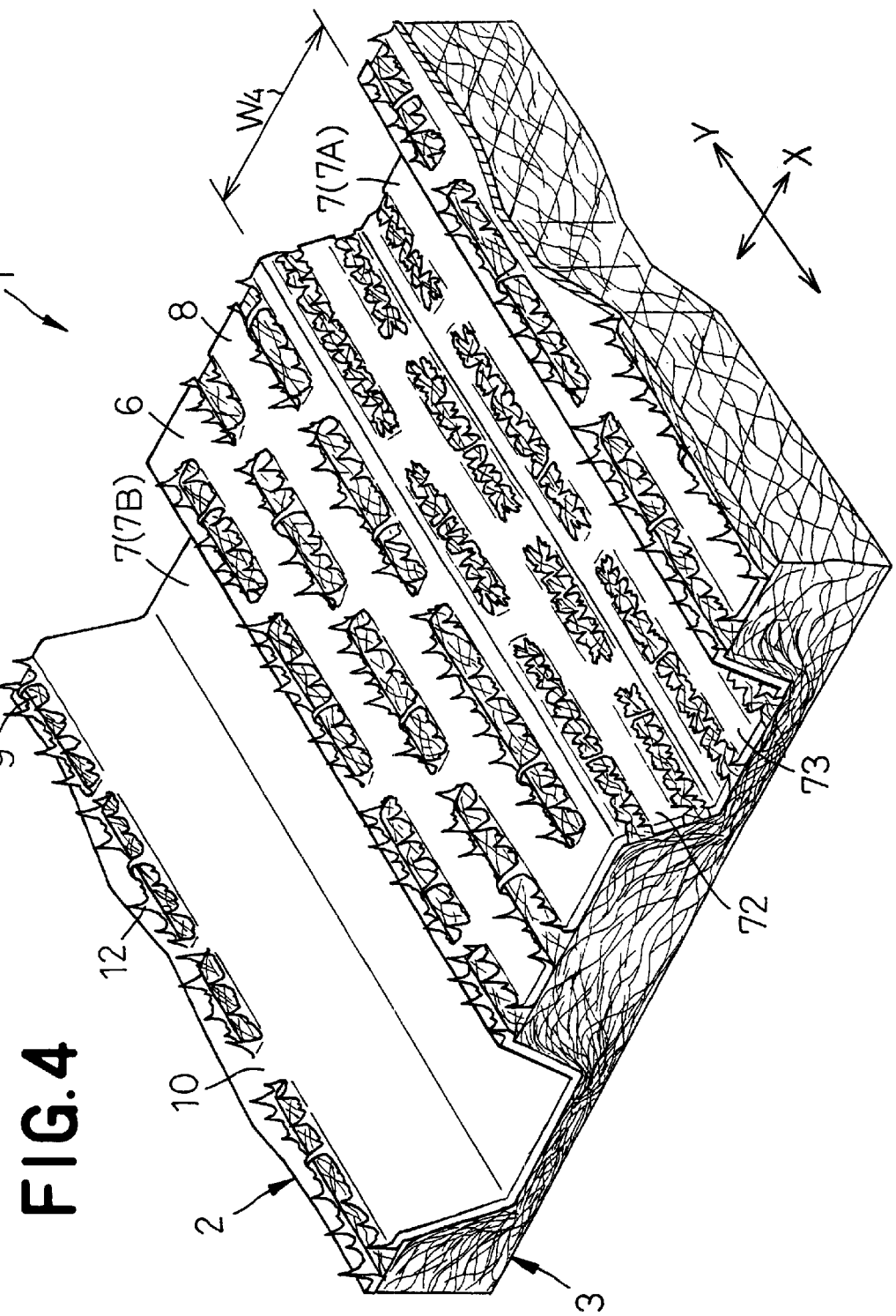
FIG. 4 is a view similar to FIG. 2 but depicting another embodiment of this invention.
Figure 5:
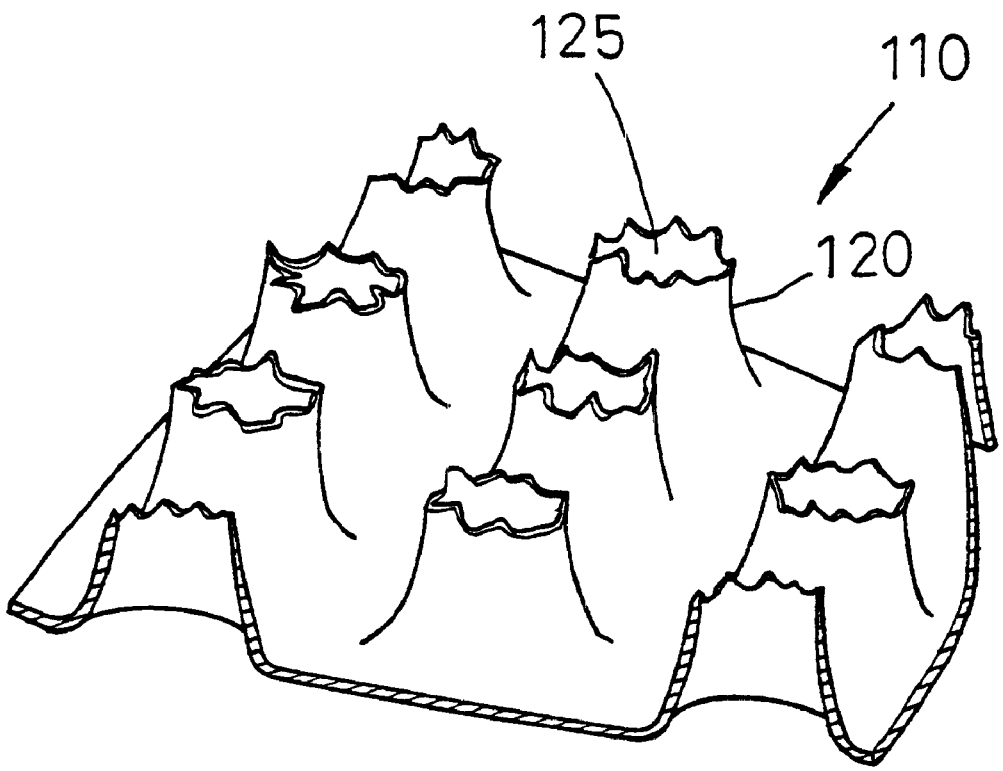
FIG. 5 is a perspective view depicting an example of the plastic sheet of prior art.

FIG. 4 is a view similar to FIG. 2 but depicting another embodiment of this invention. According to this embodiment, the individual second surface region 7 is provided in the form of a groove extending in the direction Y. The first surface region 6 and the second surface region 7 are alternately arranged and extend parallel one to another. The second surface region 7 occupies 1~50%, preferably 10~40% of the total area of the composite sheet 1 and its depth as measured from the plane zones 8 of the first surface region 6 is at least 0.1 mm. The individual second surface region 6 has a width $W_4$ of 0.2~5 mm and each pair of the adjacent individual second surface regions 7 are spaced from each other at least by 2 mm. Some 7A of the second surface regions 7 have the apertures 9 in their side walls 72 and bottom walls 73 and the other 7B provided with few or no aperture 9. In the case of the second surface regions 7A, the rising zones 12 may be present or absent along the aperture 9, if the latter is present. Similarly to the case shown by FIG. 2, the lower layer 3 has its density being relatively low under the first surface regions 6 and relatively high under the second surface regions 7. Consequently, the composite sheet 1 has its flexural rigidity higher in the direction Y than in the direction X due to the presence of the second surface regions 7. When such composite sheet 1 is used as a topsheet of sanitary napkin, the direction Y of the sheet 1 may be put in coincidence with the longitudinal direction of the napkin in order to facilitate the napkin to be transversely curved.

Without departing from the scope and spirit of this invention, the second surface regions 7 provided in the form of the grooves as shown in FIG. 4 may be oriented to extend transversely of the direction Y, i.e., transversely of the direction in which the first surface regions 6 extend. In this case, the composite sheet 1 will have its flexural rigidity relatively high in the direction in which the second surface regions 7 extend. The plurality of second surface regions 7 provided in the form of grooves may also extend so as to intersect one another.

What is claimed is:

1. A flexible composite sheet for use in a disposable garment, comprising:

a thermoplastic synthetic film having an upper and a lower surface and longitudinal and transverse directions, said thermoplastic synthetic film being about 0.001 to about 0.05 mm thick and including a plurality of substantially flat portions each being about 0.03 to about 1 mm wide, said plurality of substantially flat portions extending in parallel to one another in said longitudinal direction, said thermoplastic synthetic film further including a plurality of intermittent apertures extending in said longitudinal direction between said substantially flat portions so as to form a plurality of aperture rows extending in parallel to one another in said longitudinal direction;

pairs of said substantially flat portions having said aperture rows therebetween being interconnected by a plurality of bridge portions which extend therebetween and across said aperture rows, said bridge portions extending across the respective aperture rows are formed intermittently in the transverse direction, said bridge portions comprising two types of bridge portions including bridge portions that extend upward or downward from the upper surfaces of the substantially flat portions to the upper surfaces of the respective adjacent substantially flat portions so as to describe arcs and bridge portions that are flush with the substantially flat portions;

said intermittent apertures being defined by edges of said substantially flat portions that extend in said longitudinal direction and edges of said bridge portions which extend in said transverse direction;

said substantially flat portions being formed at least along said edges thereof that extend in said longitudinal direction with a plurality of substantially pointed tooth-shaped portions that extend upward from upper surfaces of said substantially flat portions;

a nonwoven fibrous layer having a lower surface and a substantially uniform basis weight and bonded to the lower surface of said thermoplastic synthetic resin film; and a plurality of discrete depressed areas formed by depressing discrete areas of said composite sheet downward from the upper surface of said thermoplastic synthetic resin film toward the lower surface of the nonwoven fibrous layer by a depth of at least 0.1 mm, said depressed areas having bottoms and side walls, and at least some of said plurality of intermittent apertures extending into said bottoms and into said side walls, said nonwoven fibrous layer containing thermoplastic synthetic fibers in an amount of at least 30% by weight and having a density that is higher in first regions immediately underlying said discrete depressed areas than in regions immediately surrounding said first regions.

2. The composite sheet according to claim 1, wherein said nonwoven fibrous layer has a density which progressively increases from said first regions toward regions immediately surrounding said first regions.

3. The composite sheet according to claim 1, wherein said nonwoven fibrous layer has a density of 0.01~0.3 g/cm$^3$ in said first regions and a density of 0.05~0.9 g/cm$^3$ in regions immediately surrounding said first regions.

4. The composite sheet according to claim 1, wherein said nonwoven fibrous layer has a basis weight of 5~100 g/m$^2$.

5. The composite sheet according to claim 1, wherein said nonwoven fibrous layer is formed from thermoplastic synthetic fibers having a fineness of 0.01~15 d.

6. The composite sheet according to claim 1, wherein said depressed areas occupy 1~50% of said total area of said composite sheet.

7. The composite sheet according to claim 1, wherein said tooth-shaped portions undulate in a range of height of up to 1 mm as measured from the upper surface of said thermoplastic synthetic film.

8. The composite sheet according to claim 1, where adjacent ones of said depressed areas are spaced from one another by at least 2 mm.

9. The composite sheet according to claim 1, wherein said depressed areas comprise grooves extending in said transverse direction.

* * * * *